United States Patent
Bessant et al.

(10) Patent No.: US 11,896,058 B2
(45) Date of Patent: Feb. 13, 2024

(54) AEROSOL-GENERATING SYSTEM WITH AIR QUALITY SENSOR

(71) Applicant: Philip Morris Products S.A., Neuchatel (CH)

(72) Inventors: Michel Bessant, Neuchatel (CH); Filip Tack, Neuchatel (CH)

(73) Assignee: Philip Morris Products S.A., Neuchatel (CH)

( * ) Notice: Subject to any disclaimer, the term of this patent is extended or adjusted under 35 U.S.C. 154(b) by 601 days.

(21) Appl. No.: 17/256,392

(22) PCT Filed: Jul. 9, 2019

(86) PCT No.: PCT/EP2019/068464
§ 371 (c)(1),
(2) Date: Dec. 28, 2020

(87) PCT Pub. No.: WO2020/011815
PCT Pub. Date: Jan. 16, 2020

(65) Prior Publication Data
US 2021/0145068 A1    May 20, 2021

(30) Foreign Application Priority Data

Jul. 10, 2018    (EP) .................................... 18182797

(51) Int. Cl.
*A24F 40/40*    (2020.01)
*A24F 40/51*    (2020.01)
(Continued)

(52) U.S. Cl.
CPC .............. *A24F 40/51* (2020.01); *A24F 40/20* (2020.01); *A24F 40/40* (2020.01); *A24F 40/57* (2020.01);
(Continued)

(58) Field of Classification Search
CPC .......... A24F 40/10; A24F 40/51; A24F 40/50; A24F 40/53
See application file for complete search history.

(56) References Cited

U.S. PATENT DOCUMENTS 9,155,336 B2    10/2015    Liu
11,133,692 B2 *    9/2021    Akao ..................... H02J 7/005
(Continued)

FOREIGN PATENT DOCUMENTS

CN    203776159 U    8/2014
CN    204599337 U    9/2015
(Continued)

OTHER PUBLICATIONS

Japanese Office Action dated Jun. 19, 2023 in Japanese Application 2020-570721, (with English translation), 10 pages.
(Continued)

*Primary Examiner* — Truc T Nguyen
(74) *Attorney, Agent, or Firm* — Oblon, McClelland, Maier & Neustadt, L.L.P.

(57) ABSTRACT

An aerosol-generating system, and aerosol-generating device, and a charging case for an aerosol-generating device are provided. The system includes an aerosol-generating device; an ambient air quality sensor; and a controller. The device includes a housing having a chamber to receive an aerosol-forming substrate; and a heating assembly to heat the substrate when the substrate is received in the chamber. The ambient air quality sensor is arranged to sense a property of the ambient air in the vicinity of the system and the controller is connected to the ambient air quality sensor and is configured to receive ambient air quality readings from the ambient air quality sensor and to output an ambient air quality signal based on one or more of the readings of the ambient air quality sensor.

14 Claims, 4 Drawing Sheets

(51) Int. Cl.
    *A24F 40/65*     (2020.01)
    *A24F 40/95*     (2020.01)
    *A24F 40/20*     (2020.01)
    *A24F 40/57*     (2020.01)
    *A24F 40/60*     (2020.01)
    *G01N 33/00*     (2006.01)
    *H02J 7/00*     (2006.01)
    *F24F 110/62*     (2018.01)

(52) U.S. Cl.
    CPC .............. *A24F 40/60* (2020.01); *A24F 40/65* (2020.01); *A24F 40/95* (2020.01); *G01N 33/0027* (2013.01); *H02J 7/0044* (2013.01); *F24F 2110/62* (2018.01)

(56) References Cited

U.S. PATENT DOCUMENTS

| | | | |
|---|---|---|---|
| 11,337,460 B2 * | 5/2022 | Ono | H02J 7/0042 |
| 11,399,573 B2 * | 8/2022 | Aradachi | H02J 7/0042 |
| 2005/0137491 A1 | 6/2005 | Paz et al. | |
| 2011/0265806 A1 | 11/2011 | Alarcon et al. | |
| 2013/0037041 A1 * | 2/2013 | Worm | A24F 40/46 131/329 |
| 2013/0333711 A1 | 12/2013 | Liu | |
| 2014/0000638 A1 * | 1/2014 | Sebastian | A24F 40/50 131/328 |
| 2016/0331036 A1 | 11/2016 | Cameron | |
| 2017/0033568 A1 | 2/2017 | Holzherr | |
| 2017/0224024 A1 | 8/2017 | Jochnowitz et al. | |
| 2018/0007970 A1 | 1/2018 | Sur | |
| 2018/0020729 A1 * | 1/2018 | Alarcon | G05D 23/1927 392/404 |
| 2019/0252888 A1 | 8/2019 | Holzherr | |
| 2019/0274354 A1 * | 9/2019 | Sur | A61M 15/06 |
| 2020/0006950 A1 | 1/2020 | Holzherr | |
| 2020/0221778 A1 * | 7/2020 | Trzecieski | A24F 40/10 |
| 2021/0345681 A1 * | 11/2021 | Cameron | A24F 40/53 |

FOREIGN PATENT DOCUMENTS

| | | |
|---|---|---|
| CN | 106132222 A | 11/2016 |
| CN | 106415237 A | 2/2017 |
| CN | 106793836 A | 5/2017 |
| CN | 107373779 A | 11/2017 |
| CN | 107624040 A | 1/2018 |
| CN | 107820395 A | 3/2018 |
| JP | 2013-524835 A | 6/2013 |
| JP | 2017-79747 A | 5/2017 |
| JP | 2017-518733 A | 7/2017 |
| JP | 2017-537610 A | 12/2017 |
| RU | 103 281 U1 | 4/2011 |
| RU | 2 618 436 C2 | 5/2017 |
| RU | 2 651 475 C2 | 4/2018 |
| RU | 2 656 820 C1 | 6/2018 |
| WO | WO 2015/165813 A1 | 11/2015 |
| WO | WO 2017/001520 A1 | 1/2017 |
| WO | WO 2017/182249 A1 | 10/2017 |
| WO | WO 2019/115464 A1 | 6/2019 |
| WO | WO 2019/175810 A1 | 9/2019 |

OTHER PUBLICATIONS

Combined Russian Office Action and Search Report dated Nov. 9, 2022 in Russian Patent Application No. 2020142245 (with English translation), 21 pages.
International Search Report and Written Opinion dated Jan. 24, 2020 in PCT/EP2019/066464 filed on Jun. 9, 2019.
Extended European Search Report dated Feb. 27, 2019 in European Patent Application No. 18182797.3, 10 pages.
Office Action dated Aug. 5, 2023, in Chinese Patent Application No. 201980040803.0, w/ English-languange Translation.

\* cited by examiner

AEROSOL-GENERATING SYSTEM WITH AIR QUALITY SENSOR

The invention relates to an aerosol-generating system, an aerosol-generating device of an aerosol-generating system and a charging unit of an aerosol-generating system.

Aerosol-generating systems comprising an aerosol-generating device adapted to receive an aerosol-forming substrate and generate an aerosol from the aerosol-forming substrate are known. Such systems are generally configured to heat the aerosol-forming substrate via a heating assembly to generate an aerosol which can be inhaled by a user of the system. Some systems are configured to generate an aerosol from a solid aerosol-forming substrate, typically comprising tobacco. The solid aerosol-forming substrate may be wrapped together with a filter and other elements to form a rod, similar to a conventional cigarette. Other systems are configured to generate an aerosol from a liquid aerosol-forming substrate, typically containing nicotine. The liquid aerosol-forming substrate may be contained in a disposable cartridge, which may also comprise a heating element that is supplied with power from the aerosol-generating device for heating and vapourising the substrate.

Aerosol-generating systems may be used in a variety of environmental conditions. The environmental conditions in the vicinity of the system may affect the aerosol generated by the aerosol-generating system. For example, the humidity in the vicinity of a system having a solid aerosol-forming substrate may affect the moisture content of the solid aerosol-forming substrate, which may alter the composition of the aerosol generated from the substrate. The environmental conditions in the vicinity of the system may also affect a user's perception of an aerosol generated by the system.

It would be desirable to provide an aerosol-generating system that is able to generate a consistent aerosol in a variety of environmental conditions. It would also be desirable to provide an aerosol-generating system that is adaptable for use in a variety of environmental conditions.

According to the invention there is provided an aerosol-generating system comprising: an aerosol-generating device; an ambient air quality sensor; and a controller. The aerosol-generating device comprises: a housing having a chamber for receiving an aerosol-forming substrate; and a heating arrangement for heating the aerosol-forming substrate when the aerosol-forming substrate is received in the chamber. The ambient air quality sensor is arranged to sense a property of the ambient air in the vicinity of the system, and the controller is connected to the ambient air quality sensor and is configured to receive ambient air quality readings from the ambient air quality sensor and to output an ambient air quality signal based on one or more of the readings of the ambient air quality sensor.

Advantageously, the inventors of the present invention have realised that the ambient environment in the vicinity of an aerosol-generating system may affect the aerosol-generating experience for a user. For example, variations in the humidity in the ambient environment may affect the properties of the aerosol-forming substrate and may require the temperature of the heating assembly to be adjusted in order to generate a consistent aerosol regardless of the ambient environment in which the aerosol-generating system is used. Accordingly, by monitoring properties of the ambient air in the vicinity of the system, it may be possible to improve the aerosol-generating experience for a user.

In some preferred embodiments, there is provided an aerosol-generating system comprising an aerosol-generating device, the aerosol-generating device comprising: a housing having a chamber for receiving an aerosol-forming substrate, the chamber being arranged at a proximal end of the device; a heating arrangement for heating the aerosol-forming substrate when the aerosol-forming substrate is received in the chamber; an ambient air quality sensor arranged to sense a property of the ambient air in the vicinity of the system, the ambient air quality sensor being arranged at a distal end of the device, opposite the proximal end; and a controller connected to the ambient air quality sensor and configured to receive ambient air quality readings from the ambient air quality sensor and to output an ambient air quality signal based on one or more of the readings of the ambient air quality sensor.

Advantageously, this arrangement of the ambient air quality sensor may position the ambient air quality sensor as far as possible away from aerosol-generating portion of the device, at the chamber and the heating assembly. This may reduce the likelihood that aerosol generated by the aerosol-generating device may affect the ambient air quality readings from the ambient air quality sensor.

In some preferred embodiments, there is provided an aerosol-generating system comprising: an aerosol-generating device and a charging unit. The aerosol-generating device comprises: a housing having a chamber for receiving an aerosol-forming substrate; a heating arrangement for heating the aerosol-forming substrate when the aerosol-forming substrate is received in the chamber; and a power supply housed in the housing. The charging unit comprises: power transfer circuitry for transferring power to the power supply of the aerosol-generating device; an ambient air quality sensor arranged to sense a property of the ambient air in the vicinity of the system; and a controller connected to the ambient air quality sensor, configured to receive ambient air quality readings from the ambient air quality sensor and configured to output an ambient air quality signal based on one or more of the readings of the ambient air quality sensor.

Advantageously, providing the ambient air quality sensor in a charging unit of the aerosol-generating system, rather than in the aerosol-generating device, may position the ambient air quality sensor even further away from the aerosol-generating portion of the system, at the chamber and the heating assembly of the aerosol-generating device. This may further reduce the likelihood that aerosol generated by the aerosol-generating device may affect the ambient air quality readings from the ambient air quality sensor.

As used herein, the term "ambient air" is used to mean the air in the ambient environment around the system. In other words, the term "ambient air" is used to mean the air immediately surrounding the system. The term "ambient air" is not intended to cover the mixture of air and aerosol inside the chamber of the device when aerosol-forming substrate is received in the chamber and is heated by the heating assembly to generate an aerosol.

As used herein, the term "ambient air quality sensor" is used to refer to a sensor that is configured to sense one or more properties of the ambient air in the vicinity of the system. In particularly preferred embodiments of the invention, the ambient air quality sensor is configured to sense one or more of: carbon monoxide; volatile organic compounds; humidity, in particular relative humidity; carbon dioxide; fine particulate matter; nitrogen dioxide; dioxygen; pressure; and nicotine.

The ambient air quality sensor may comprise one or more gas sensors for detecting the presence of one or more gases in the ambient environment around the system. In particular, the one or more gas sensors may be configured to detect the concentration of one or more gases in the ambient air surrounding the system. Preferably, the one or more gas sensors may be configured to sense one or more of: carbon monoxide, volatile organic compounds, carbon dioxide; nitrogen dioxide; dioxygen; and nicotine. Preferably, the aerosol-generating system comprises an ambient air quality sensor configured to sense carbon monoxide in the ambient air surrounding the system.

The one or more gas sensors may be any suitable type of gas sensor. Suitable types of gas sensor include: electrochemical gas sensors, such as chemical field-effect transistors; chemical resistive sensors; metal oxide semiconductor (MOS) sensors; catalytic sensors (pellistors); microcantilever array sensors; surface acoustic wave (SAW) sensors; photoionization detectors (PIDs); and infrared sensors.

Some exemplary suitable gas sensors which are currently available include: SGP30 and SGPC3 from Sensirion AG; CDM7160-000 and TGS2602 from FIGARO USA., INC; and MiCS-VZ-89TE from SGX Sensortech Limited.

The ambient air quality sensor may comprise one or more sensors for sensing volatile organic compounds (VOCs). As used herein, the term "organic compound" means any compound containing at least the element carbon and one or more of hydrogen, halogens, oxygen, sulphur, phosphorus, silicon or nitrogen, with the exception of carbon oxides and inorganic carbonates and bicarbonates. As used herein, the term "volatile organic compound (VOC)" means any organic compound having at 293.15 Kelvin (K) a vapour pressure of 0.01 kilopascal (kPa) or more, or having a corresponding volatility under the particular conditions of use. The definitions of "organic compound" and "volatile organic compound" used herein are taken from directive 2010/75/EU of the European parliament and of the council of 24 Nov. 2010 on industrial emissions (integrated pollution prevention and control).

The one or more volatile organic compound sensors may be any suitable type of sensor. For example, suitable VOC sensors include: electrochemical gas sensors, such as chemical field-effect transistors; chemical resistive sensors; metal oxide semiconductor (MOS) sensors; catalytic sensors (pellistors); microcantilever array sensors; surface acoustic wave (SAW) sensors; photoionization detectors (PIDs); and infrared sensors.

Some exemplary suitable VOC sensors which are currently available include: SGP30 and SGPC3 from Sensirion AG; TGS2602 from FIGARO USA., INC; and MiCS-VZ-89TE from SGX Sensortech Limited.

The ambient air quality sensor may comprise one or more humidity sensors. As used herein, the term "humidity" may refer to absolute humidity, relative humidity or specific humidity. As used herein, the term "absolute humidity" refers to the mass of water vapour in a unit volume of air, which may be expressed in grams per cubic meter. As used herein, the term "relative humidity" refers to the ratio of the actual vapour density and the saturation vapour density at a given temperature, which may be expressed as a percentage. Put in another way, the term "relative humidity" refers to the ratio of the partial pressure of water vapour in a mixture at a given temperature to the equilibrium vapour pressure of water over a flat surface of pure water at that given temperature. As used herein, "specific humidity" refers to the ratio of the mass of water vapour to the total mass of the mixture of water vapour and air, which may be expressed in grams of vapour per kilogram of air.

The one or more humidity sensors may be any suitable type of sensor. For example, suitable humidity sensors include: capacitive humidity sensors; resistive humidity sensors; and thermal conductivity based humidity sensors.

Some exemplary suitable humidity sensors which are currently available include: SHT3x, SHTW2, SHTC3 and SHT7x humidity sensors from Sensirion AG.

The one or more humidity sensors may be combined with one or more temperature sensors. In particular, where the one or more humidity sensors are configured to sense the relative humidity of the air in the vicinity of the aerosol-generating system, the one or more humidity sensors also comprise a temperature sensor. The one or more temperature sensors may be any suitable type of temperature sensor, such as: bandgap temperature sensors; resistance temperature detectors (RTDs); thermocouples; thermistors, particularly negative temperature coefficient (NTC) thermistors; and semiconductor temperature sensors.

The ambient air quality sensor may comprise one or more sensors configured to sense fine particulate matter in the ambient air in the vicinity of the aerosol-generating system. As used herein, the term "fine particulate matter" refers to particles and suspended in the ambient air in the vicinity of the aerosol-generating system. In particular, particulate matter comprises inhalable particles, with diameters that are generally 10 micrometres and smaller (PM10) and fine inhalable particles, with diameters that are generally 2.5 micrometres and smaller (PM2.5).

More specifically, as used herein, fine particulate matter includes PM10, which refers to particulate matter which passes through a size-selective inlet with a 50% efficiency cut-off at 10 μm aerodynamic diameter. The reference method for the sampling and measurement of PM10 is that described in EN 12341:1999 'Air Quality—Determination of the PM10 fraction of suspended particulate matter—Reference method and field test procedure to demonstrate reference equivalence of measurement methods'. As used herein, fine particulate matter also includes PM2.5, which refers to particulate matter which passes through a size-selective inlet with a 50% efficiency cut-off at 2.5 μm aerodynamic diameter. The reference method for the sampling and measurement of PM2.5 is that described in EN 14907:2005 'Standard gravimetric measurement method for the determination of the PM2.5 mass fraction of suspended particulate matter'. The definitions of PM10 and PM2.5 used herein are taken from Directive 2008/50/EC of the European Parliament and of the Council of 21 May 2008 on ambient air quality and cleaner air for Europe.

The one or more fine particulate matter sensors may be any suitable type of particulate matter sensor, such as: resistive particulate matter sensors; thermophoretic particulate matter sensors; laser-based light scattering particulate matter sensors.

The ambient air quality sensor may comprise one or more ambient pressure sensors. Ambient pressure readings may be particularly advantageous in combination with humidity and temperature readings, as the combination of humidity, temperature and pressure readings may improve the reliability of the humidity determination.

The one or more ambient pressure sensors may be any suitable type of pressure sensor, such as: capacitive pressure sensors; piezoelectric pressure sensors; and piezoresistive pressure sensors. The one or more pressure sensors may be absolute pressure sensors or differential pressure sensors.

The one or more ambient air quality sensors may comprise at least one of: an electrochemical sensor; a chemical resistive sensor; a Metal Oxide Semiconductor (MOS) sensor; a catalytic sensor; and a mass spectrometer.

The one or more ambient air quality sensors may be electro-mechanical devices. The one or more ambient air quality sensors may be any of: a mechanical device, an optical device, an opto-mechanical device and a microelectromechanical systems (MEMS) based sensor. Preferably, the one or more ambient air quality sensors are microelectromechanical systems (MEMS) based sensors.

The one or more ambient air quality sensors may consist of a gas sensor. The one or more ambient air quality sensors may consist of a gas sensor configured to sense carbon monoxide. The one or more ambient air quality sensors may consist of a gas sensor configured to sense carbon dioxide. The one or more ambient air quality sensors may consist of a gas sensor configured to sense nicotine. The one or more ambient air quality sensors may consist of a gas sensor configured to sense carbon monoxide and a gas sensor configured to sense carbon dioxide. The one or more ambient air quality sensors may consist of a gas sensor configured to sense carbon monoxide and a gas sensor configured to sense nicotine. The one or more ambient air quality sensors may consist of a gas sensor configured to sense carbon dioxide and a gas sensor configured to sense nicotine. The one or more ambient air quality sensors may consist of a gas sensor configured to sense carbon monoxide, a gas sensor configured to sense carbon dioxide, and a gas sensor configured to sense nicotine.

The one or more ambient air quality sensors may consist of a sensor for sensing VOCs. The one or more ambient air quality sensors may consist of a gas sensor and a sensor for sensing VOCs. The one or more ambient air quality sensors may consist of a sensor for sensing fine particulate matter. The one or more ambient air quality sensors may consist of a gas sensor and a sensor for sensing fine particulate matter. The one or more ambient air quality sensors may consist of a gas sensor, a sensor for sensing VOCs, and a sensor for sensing fine particulate matter.

The one or more ambient air quality sensors may consist of a gas sensor and a humidity sensor. The one or more ambient air quality sensors may consist of a gas sensor and a humidity sensor, including an ambient temperature sensor. The one or more ambient air quality sensors may consist of a humidity sensor and a pressure sensor. The one or more ambient air quality sensors may consist of a humidity sensor, including an ambient temperature sensor, and a pressure sensor. The one or more ambient air quality sensors may consist of a gas sensor, a humidity sensor, and a pressure sensor. The one or more ambient air quality sensors may consist of a gas sensor, a humidity sensor, including an ambient temperature sensor, and a pressure sensor.

The aerosol-generating system comprises a controller. The controller is electrical circuitry connected to the ambient air quality sensor. The controller is configured to receive ambient air quality readings from the ambient air quality sensor and to output an ambient air quality signal based on one or more of the readings of the ambient air quality sensor.

The controller may comprise a microprocessor, which may be a programmable microprocessor, a microcontroller, or an application specific integrated chip (ASIC) or other electronic circuitry capable of providing control. The controller may comprise further electronic components. In some embodiments, the controller may comprise the ambient air quality sensor.

Advantageously, in some embodiments the aerosol-generating device may comprise the ambient air quality sensor. In some embodiments, the aerosol-generating device may comprise the controller. In some embodiments, the ambient air quality sensor may be arranged on or in the housing of the device. In some embodiments, the controller may be arranged on or in the housing of the device. Advantageously, arranging the ambient air quality sensor on or in the housing of the aerosol-generating device may ensure that the ambient air quality readings are representative of the ambient environment in the vicinity of the device. Such an arrangement positions the ambient air quality sensor in the same ambient environment as the chamber of the device, the heating assembly and the aerosol-forming substrate received in the chamber.

In some preferred embodiments, the ambient air quality sensor is arranged within the housing of the device. In these preferred embodiments, the housing of the device may comprise at least one opening to enable ambient air to enter the housing to reach the ambient air quality sensor. The opening may be arranged adjacent or close to the ambient air quality sensor. In some embodiments, the housing may comprise a first opening to enable ambient air to enter the housing to reach the ambient air quality sensor and a second opening to enable ambient air to exit the housing. An airflow pathway may be formed through the housing from the first opening, over the ambient air quality sensor, to the second opening. The airflow pathway may enable a flow of ambient air over the ambient air quality sensor.

The ambient air quality sensor is not arranged in or around the chamber for receiving the aerosol-forming substrate. The ambient air quality sensor is not arranged in or around the chamber for receiving the aerosol-forming substrate because the aerosol generated by the aerosol-generating system is generated in and around the chamber. Therefore, the air in and around the chamber for receiving the aerosol-forming substrate is not generally representative of the ambient air surrounding the system.

The ambient air quality sensor may be spaced from the chamber for receiving the aerosol-forming substrate. In some embodiments the aerosol-generating device is elongate, having a longitudinal axis, and the ambient air quality sensor is spaced from the chamber for receiving the aerosol-forming substrate along the longitudinal axis.

In some embodiments, the aerosol-generating device may comprise a proximal end and a distal end, opposite the proximal end. As used herein, the terms 'proximal' and 'distal' are used to describe relative positions of components, or portions of components, of aerosol-generating devices and charging units. The chamber of the device may be arranged at the proximal end of the device. The ambient air quality sensor may be arranged at the distal end of the device. Advantageously, this arrangement may position the ambient air quality sensor as far as possible away from aerosol-generating portion of the device, at the chamber and the heating assembly. This may reduce the likelihood that aerosol generated by the device may affect the ambient air quality readings from the ambient air quality sensor.

The ambient air quality sensor may be substantially isolated from aerosol-generating regions of the aerosol-generating device. For example, the ambient air quality sensor may be substantially isolated from the chamber of the aerosol-generating device. Where a charging unit comprises the ambient air quality sensor, and the charging unit comprises a chamber for receiving the aerosol-generating device, the ambient air quality sensor may be substantially isolated from the chamber for receiving the aerosol-generating device. In other words, the ambient air quality sensor may be substantially isolated from the aerosol-generating device when the aerosol-generating device is received in the chamber of the charging unit.

Substantially isolating the ambient air quality sensor from the aerosol-generating regions of the aerosol-generating device may ensure that aerosol generated by the aerosol-generating system does not come into contact with the ambient air quality sensor.

The aerosol-generating system may comprise a first airflow pathway through which air is drawn into the aerosol-generating system, though an aerosol-generating region of the system, and out of the aerosol-generating system to a user. Such an airflow pathway may enable aerosol generated by the aerosol-generating system to be entrained in airflow through the first airflow pathway, and delivered to a user through the first airflow pathway. The first airflow pathway may comprise the chamber of the aerosol-generating device. The ambient air quality sensor may be substantially isolated from the first airflow pathway.

The ambient air quality sensor may be substantially isolated from the aerosol-generating regions of the aerosol-generating device in any suitable manner. For example, one or more gas impermeable barriers may be arranged between the ambient air quality sensor and the first airflow pathway. For example, the ambient air quality sensor may be positioned at the opposite end of the aerosol-generating device to the chamber of the aerosol-generating device. For example, the ambient air quality sensor may be arranged in a second airflow pathway of the aerosol-generating system, the second airflow pathway being substantially isolated from the first airflow pathway.

Where the ambient air quality sensor is provided in a charging unit having a chamber for receiving the aerosol-generating device, the ambient air quality sensor may be arranged outside of the chamber for receiving the aerosol-generating device. The ambient air quality sensor may be arranged at the opposite end of the charging unit to the chamber for receiving the aerosol-forming substrate.

In preferred embodiments, the aerosol-generating device comprises a power supply configured to supply power to the heating assembly. Preferably the power supply is a DC power supply. The power supply may be housed within the housing of the device. Typically, the power supply is a battery, such as a lithium iron phosphate battery. However, in some embodiments the power supply may be another form of charge storage device, such as a capacitor. The power supply may require recharging and may have a capacity that allows for the storage of enough energy for one or more user operations, for example one or more aerosol-generating experiences. For example, the power supply may have sufficient capacity to allow for continuous heating of an aerosol-forming substrate for a period of around six minutes, corresponding to the typical time taken to smoke a conventional cigarette, or for a period that is a multiple of six minutes. In another example, the power supply may have sufficient capacity to allow for a predetermined number of puffs or discrete activations of the heating assembly.

Preferably, the aerosol-generating device may further comprise power supply control circuitry connected to the power supply and to the heating assembly. The power supply control circuitry is configured to control the supply of power from the power supply to the heating assembly. The power supply control circuitry is electric circuitry that is configured to regulate a supply of current to the heating assembly. Current may be supplied to the heating assembly continuously following activation of the device or may be supplied intermittently, such as on a puff by puff basis.

The power supply control circuitry may be configured to control the power supplied from the power supply to the heating assembly in any suitable manner. In some preferred embodiments, the power supply control circuitry may be configured to supply power from the power supply to the heating assembly in a pulsed power signal. In these preferred embodiments, the power supply control circuitry may be configured to control the power supplied to the heating assembly by frequency modulation or by pulse width modulation of the pulsed power signal.

Where the aerosol-generating device comprises the controller, the power supply control circuitry may be part of the controller or may be separate electrical circuitry connected to the controller. Where the power supply control circuitry is connected to the controller, the power supply control circuitry is configured to receive the ambient air quality signal from the controller and control the supply of power from the power supply to the heating assembly based on the ambient air quality signal. In this way, the controller may be configured to control the power supplied to the heating assembly based on one or more of the ambient air quality readings.

In some preferred embodiments, the power supply control circuitry is part of the controller. In these preferred embodiments, the controller may be configured to control the power supplied from the power supply to the heating assembly based on one or more ambient air quality readings. In these embodiments, the power supply circuitry may output an ambient air quality signal in the form of a power signal to the heating assembly.

The controller may be configured to decrease the power supplied to the heating assembly when the ambient air quality readings indicate that the ambient air quality meets one or more predetermined ambient air quality conditions. For example, the controller may be configured to decrease the power supplied to the heating assembly when the ambient air quality readings exceed a predetermined threshold. Decreasing the power supplied to the heating assembly may decrease the amount of aerosol generated by the system.

In some embodiments, the control circuitry may be configured to increase the power supplied from the power supply to the heating assembly when the ambient air quality readings indicate that the ambient air quality meets a certain air quality condition or exceeds a certain quality threshold.

In an exemplary embodiment, the controller may be configured to increase the power supplied from the power supply to the heating assembly when the ambient air quality signal indicates that the humidity is above a certain humidity threshold. The controller may be configured to increase the power supplied from the power supply to the heating assembly for an initial predetermined period of time, such that any addition moisture in the substrate due to the humidity is vaporised before a user begins an aerosol-generating experience. In another exemplary embodiment, the controller may be configured to decrease the power supplied from the power supply to the heating assembly when the ambient air quality signal indicates that the concentration of one or more gases, such as carbon monoxide and carbon dioxide, exceeds a predetermined concentration threshold.

The controller may be configured to store one or more predetermined ambient air quality conditions or ambient air quality thresholds. The controller may be configured to store one or more predetermined ambient air quality conditions or ambient air quality thresholds on a memory of the controller. The one or more predetermined ambient air quality conditions or ambient air quality thresholds may be stored in a lookup table.

Any suitable ambient air quality conditions or thresholds may be stored on a memory of the controller.

Suitable carbon monoxide (CO) concentration thresholds may include: at least 1 parts per million (ppm), at least 5 ppm, at least 10 ppm, at least 20 ppm, at least 30 ppm, at least 40 ppm, at least 50 ppm, at least 60 ppm, at least 70 ppm, at least 80 ppm, at least 90 ppm, at least 100 ppm, at least 150 ppm, at least 200 ppm of carbon monoxide in the ambient air.

Suitable PM2.5 particulate matter concentration thresholds may include: at least 5 micrograms per metre cubed, at least 7 micrograms per metre cubed, at least 10 micrograms per metre cubed, at least 12 micrograms per metre cubed, at least 15 micrograms per metre cubed, at least 20 micrograms per metre cubed, at least 25 micrograms per metre cubed and at least 30 micrograms per metre cubed of PM2.5 in the ambient air. Suitable PM10 particulate matter concentrations may include: at least 10 micrograms per metre cubed, at least 15 micrograms per metre cubed, at least 20 micrograms per metre cubed, at least 25 micrograms per metre cubed, at least 30 micrograms per metre cubed, at least 40 micrograms per metre cubed, at least 50 micrograms per metre cubed and at least 60 micrograms per metre cubed of PM10 in the ambient air.

Suitable nitrogen dioxide (NO2) concentration thresholds may include: at least 20 micrograms per metre cubed, at least 25 micrograms per metre cubed, at least 30 micrograms per metre cubed, at least 35 micrograms per metre cubed, at least 40 micrograms per metre cubed, at least 45 micrograms per metre cubed, at least 50 micrograms per metre cubed, at least 60 micrograms per metre cubed, at least 100 micrograms per metre cubed, at least 150 micrograms per metre cubed and at least 200 micrograms per metre cubed of nitrogen dioxide in the ambient air.

Suitable carbon dioxide (CO2) concentration thresholds may include: at least 350 ppm, at least 500 ppm, at least 750 ppm, at least 1000 ppm, at least 1500 ppm, at least 2000 ppm, at least 3000 ppm, at least 4000 ppm, at least 5000 ppm, at least 5000 ppm, at least 6000 ppm of carbon dioxide in the ambient air.

As a first example, in some embodiments the control circuitry may be configured to supply a decreased power from the power supply to the heating assembly when it is determined that the concentration of carbon monoxide in the ambient air is at least 1 ppm. In these embodiments, the control circuitry may be further configured to prevent power from being supplied from the power supply to the heating assembly when it is determined that the concentration of carbon monoxide in the ambient air is at least 70 ppm.

As a second example, in some embodiments the control circuitry may be configured to supply a decreased power from the power supply to the heating assembly when it is determined that the concentration of nitrogen dioxide in the ambient air is at least 25 ppm. In these embodiments, the control circuitry may be further configured to prevent power from being supplied from the power supply to the heating assembly when it is determined that the concentration of nitrogen dioxide in the ambient air is at least 150 ppm.

In some embodiments, the power supply control circuitry may be configured to supply a constant average power to the heating assembly over an aerosol-generating experience. In some preferred embodiments, the power supply control circuitry is configured to supply power from the power supply to the heating assembly in a predetermined power profile that varies with time during an aerosol-generating experience. For example, the power supply control circuitry may be configured to gradually increase the power supplied to the heating assembly from an initial power to an operating power, over a preheating time period, and subsequently maintain the power supplied to the heating assembly at a constant average power. The power supply control circuitry may be configured to raise the power supplied to the heating assembly from an initial power to a preheating power over an initial preheating time period and to subsequently reduce the power to an operating power that is less than the preheating power. The power supply control circuitry may be configured to reduce the power supplied to the heating assembly over time during an operating period, when aerosol is being generated.

When the ambient air quality readings from the ambient air quality sensor indicate that the ambient air quality is within a normal range, the controller may be configured to supply a normal power profile to the heating assembly.

When the ambient air quality sensor includes a humidity sensor and the ambient air quality readings indicate that the humidity of the ambient air is above a predetermined humidity threshold, the controller may be configured to increase the power supplied to the heating assembly during a preheating time period. This may raise the temperature of the aerosol-forming substrate more rapidly in a humid ambient environment to vapourise any additional water content in the substrate resulting from the humid environment during the preheating time period. For example, the controller may be configured to increase the power supplied to the heating assembly during an initial preheating time period to increase the temperature of the heating assembly by about 10 degrees above a normal preheating temperature. This may enable the system to generate an aerosol after the preheating time period that is consistent with an aerosol generated in a less humid environment. After the preheating time period, the controller may be configured to supply a normal operating power to the heating assembly.

When the ambient air quality sensor includes a carbon monoxide sensor and the ambient air quality readings indicate that the carbon monoxide level is above a predetermined carbon monoxide threshold, the controller may be configured to reduce the power supplied to the heating assembly during an operating period to reduce the volume of aerosol generated by the aerosol-generating system.

In some embodiments, the controller may be configured to monitor the power supplied to the heating assembly during an aerosol-generating experience and maintain the power supplied to the heating assembly at a target power profile. The controller may be configured to control the target power profile based on one or more readings from the ambient air quality sensor.

In some embodiments, the controller may be configured to monitor another property of the power control circuitry or the heating assembly, such as the resistance of the heating assembly, during an aerosol-generating experience and control the power supplied to the heating assembly to maintain the property of the heating assembly at a target value or profile. For example, the control circuitry may be configured to monitor a resistance of the heating assembly and control the power supplied to the heating assembly to maintain the resistance of the heating assembly at the target resistance profile. The control circuitry may be configured to adjust the target profile based on one or more readings from the ambient air quality sensor.

In some preferred embodiments, the power supply control circuitry is configured to compare the ambient air quality readings from the ambient air quality sensor to a predetermined ambient air quality condition. The predetermined ambient air quality condition may be a predetermined threshold or a predetermined range. The predetermined ambient air quality condition may be stored on a memory of the controller. The controller may be further configured to substantially prevent or inhibit the supply of power from the power supply to the heating assembly when one or more ambient air quality readings are outside of the predetermined ambient air quality condition. In other words, the controller may be configured to stop the supply of power from the power supply to the heating assembly when one or more ambient air quality readings are outside of the predetermined range or exceed a predetermined threshold. Advantageously, this may ensure that a user does not receive an undesirable aerosol-generating experience resulting from the ambient environment.

For example, the ambient air quality sensor may comprise a carbon monoxide gas sensor, and the controller may be configured to prevent power from being supplied to the heating assembly when one or more readings from the ambient air quality sensor indicate that the concentration of carbon monoxide in the ambient air is above a predetermined carbon monoxide concentration threshold.

In some embodiments, the system further comprises a charging unit. The charging unit comprises power transfer circuitry for transferring power to the power supply of the aerosol-generating device. The power transfer circuitry may be any suitable type of circuitry.

The power transfer circuitry may comprise wired power transfer circuitry. In these embodiments, the charging unit comprises an electrical connector and the aerosol-generating device comprises a complimentary electrical connector configured to electrically engage with the electrical connector of the charging unit.

The power transfer circuitry may comprise wireless power transfer circuitry. In these embodiments, the charging unit may comprise a first inductor coil and the aerosol-generating device may comprise a second inductor coil configured to couple with the first inductor coil for the transfer of power between the first inductor coil and the second inductor coil.

In some embodiments, the charging unit may comprise the ambient air quality sensor. In these embodiments, the charging unit may comprise the controller. The ambient air quality sensor may be arranged on or in the charging unit. The controller may be arranged on or in the charging unit. Advantageously, the size of the charging unit may be greater than the size of the aerosol-generating device, which may enable a larger ambient air quality sensor with a greater number of sensors to be provided in the charging unit than in the aerosol-generating device.

In some preferred embodiments, the charging unit is a charging case having a chamber for receiving the aerosol-generating device. The chamber may be sized and shaped to receive an aerosol-generating device.

The charging case preferably comprises a power supply housed in the housing. Preferably the power supply is a DC power supply. Typically, the power supply is a battery, such as a lithium iron phosphate battery. However, in some embodiments the power supply may be another form of charge storage device, such as a capacitor. The power supply may require recharging and may have a capacity that allows for the storage of enough energy to charge the power supply of the aerosol-generating device a plurality of times, for example, 10 or 20 times.

The charging unit may further comprise the power transfer circuitry housed in the housing. The power transfer circuitry may be arranged to transfer power from the power supply of the charging case to the power supply of the aerosol-generating device when the aerosol-generating device is received in the chamber of the charging case.

In some preferred embodiments, the ambient air quality sensor is arranged within the housing of the charging case. In these preferred embodiments, the housing of the charging case may comprise at least one opening to enable ambient air to enter the housing to reach the ambient air quality sensor. The opening may be arranged adjacent or close to the ambient air quality sensor. In some embodiments, the housing may comprise a first opening to enable ambient air to enter the housing to reach the ambient air quality sensor and a second opening to enable ambient air to exit the housing. An airflow pathway may be formed through the housing from the first opening, over the ambient air quality sensor, to the second opening. The airflow pathway may enable a flow of ambient air over the ambient air quality sensor.

The ambient air quality sensor is not arranged in or around the chamber for receiving the aerosol-generating device. The ambient air quality sensor is not arranged in or around the chamber for receiving the aerosol-generating device because the air in and around the chamber for receiving the aerosol-generating device is not generally representative of the ambient air surrounding the system.

The ambient air quality sensor may be spaced from the chamber for receiving the aerosol-generating device.

In some embodiments, the charging case may comprise a proximal end and a distal end, opposite the proximal end. The chamber of the charging case may be open at the proximal end of the charging case. The chamber of the charging case may be closed at the proximal end of the charging case. The ambient air quality sensor may be arranged at the distal end of the charging case. Advantageously, this arrangement may position the ambient air quality sensor as far as possible away from aerosol-generating portion of the aerosol-generating device, when the aerosol-generating device is received in the chamber of the charging case. This may reduce the likelihood that aerosol generated by the device may affect the ambient air quality readings from the ambient air quality sensor.

In some particularly preferred embodiments, both the aerosol-generating device and the charging unit may comprise an ambient air quality sensor. The aerosol-generating device may comprise a first ambient air quality sensor and the charging unit may comprise a second ambient air quality sensor.

In embodiments where the aerosol-generating system comprises a charging case and the aerosol-generating device comprises an ambient air quality sensor, the controller may be configured to prevent the ambient air quality sensor of the aerosol-generating device from taking ambient air quality readings when the aerosol-generating device is received in the chamber of the charging case. This may be advantageous, as the air inside the chamber of the charging case may not be representative of the ambient air in the vicinity of the system. This may particularly apply where the aerosol-generating device is configured to perform a cleaning cycle when received in the charging case involving supplying power to the heating assembly to burn off residue in the chamber of the device by pyrolysis.

In some embodiments, the aerosol-generating system further comprises a display connected or connectable to the controller. The display may be configured to receive the ambient air quality signal from the controller and display ambient air quality information based on the ambient air quality signal.

Providing such a display may enable a user's interaction with the system to be more efficient and more effective. For example, in some embodiments the system may be configured such that a user can alter one or more settings of the device, such as the temperature to which the heating assembly is heated and the duration of heating, so that the user can alter the aerosol-generating experience. In these embodiments, the provision of a display configured to display ambient air quality information may enable the user to quickly and easily determine the potential settings that may be adjusted to ensure that their specific aerosol-generating experience requirements are met by the system.

The display is preferably a touchscreen device further configured to receive a user input. Preferably the touchscreen is configured to enable the user to adjust one or more settings of the aerosol-generating device.

The display may be any suitable type of display, such as a liquid crystal display (LCD) or an LED display. In some embodiments, the system may comprise a graphical user interface (GUI). The graphical user interface may comprise a touchscreen.

The ambient air quality signal output by the controller to the display may include suggested actions for a user based on the one or more ambient air quality readings. For example, if the ambient air quality readings indicate a poor ambient air quality, such as a concentration of fine particulate matter above a predetermined threshold, the ambient air quality signal may include a suggested action of opening a window or move to a new location before beginning the aerosol-generating experience. The suggested action may be displayed on the display for the user to see.

In preferred embodiments comprising a charging case, the charging case comprises a display connected to or connectable to the controller and configured to receive the ambient air quality signal from the controller and display ambient air quality information based on the ambient air quality signal.

In some preferred embodiments, the aerosol-generating system may further comprise an ambient air quality alarm. In these embodiments, the controller may be configured to output the ambient air quality signal to the ambient air quality alarm under certain conditions. For example, the controller may be configured to compare the one or more ambient air quality readings from the ambient air quality sensor to one or more predetermined thresholds or predetermined conditions. The controller may be further configured to output the ambient air quality signal to the alarm to activate the alarm when the comparison indicates that the one or more ambient air quality readings exceed a predetermined threshold or do not meet a predetermined condition.

The aerosol-generating device may comprise the alarm. In embodiments comprising a charging unit, the charging unit may comprise the alarm. The charging unit and the aerosol-generating device may both comprise an alarm. The charging unit and the aerosol-generating device may have the same type of alarm. The charging unit and the aerosol-generating device may have different types of alarm.

The alarm may be any suitable type of alarm. In some embodiments, the alarm may be a visual alarm, such as one or more LEDs or a particular message displayed on a display of the system. In some embodiments, the alarm may be an audible alarm, such as a buzzer or a loudspeaker.

In some preferred embodiments, the controller is configured to communicate the ambient air quality signal over a communications link with an external device or server. The external device may be any suitable external device, such as a personal computer, laptop, tablet computer or smartphone. The external server may be a remote server. In some embodiments, the system may be configured to communicate with a Cloud server over the internet.

The communications link is preferably suitable for flow of data between the aerosol-generating system and the external device or server. The communications link may be suitable for flow of data from the aerosol-generating system to the external device or server. The communications link may be suitable for flow of data from the external device or server to the aerosol-generating system. Preferably, the communications link is suitable for bi-directional flow of data from the aerosol-generating system to the external device or server and from the external device or server to the aerosol-generating system.

In some embodiments, the communications link is a wired communication link. In some embodiments, the communications link is a wireless communication link. Preferably, the communications link operates under an interface standard. An interface standard is a standard that describes one or more functional characteristics, such as code conversion, line assignments, or protocol compliance, or physical characteristics, such as electrical, mechanical, or optical characteristics, necessary to allow the exchange of information between two or more systems or pieces of equipment. Examples of suitable interface standards for the communications link include, but are not limited to, the Recommended Standard 232 (RS-232) family of standards; Universal Serial Bus (USB); Bluetooth®; FireWire (a brand name of Apple, Inc. for their IEEE 1394 interface), IrDA (Infrared Data Association—a communications standard for the short-range exchange of data by Infrared light); ZigBee (a specification based on the IEEE 802.15.4 standard for wireless personal area networks) and other Wi-Fi standards.

Preferably, the controller includes a communication interface such as, for example, at least a telemetry circuit and an antenna, for bidirectional communication with other external devices such as servers, network devices, personal computers, other aerosol-generating systems having communication interfaces and the like, and with other networks such as the internet and the like. More specifically, data and commands may be transmitted and received during uplink or downlink telemetry between the aerosol-generating system and other external devices and/or networks using the communication interface. In at least one embodiment, the communication interface is a wireless interface using one or more wireless (e.g., radio frequency) data transmission protocols such as, e.g., Bluetooth®, WI-FI, any protocol in the ultra-high frequency (UHF) band, any protocol in the super high frequency (SHF) band, low frequencies, etc.

In some embodiments the aerosol-generating device comprises a controller having a communication interface. In some embodiments comprising a charging unit, the charging unit comprises a controller having a communication interface. In some embodiments the aerosol-generating device comprises a first controller having a first communication interface and the charging unit comprise a second controller having a second communication interface.

In some embodiments, the controller is configured to communicate the air quality signal from the aerosol-generating device to the charging unit over a communications link. In some embodiments, the controller is configured to communicate the air quality signal from the charging unit to the aerosol-generating device over a communications link. In some embodiments, the communications link is suitable for bi-directional flow of data between the aerosol-generating device and charging unit. In some embodiments, the aerosol-generating device comprises a first controller having a first communication interface, the charging unit comprises a second controller having a second communication interface and a the first and second controllers are configured to communicate the ambient air quality signal over a communications link between the first and second communication interfaces. Preferably, the communications link is suitable for bi-directional flow of data between the aerosol-generating device and the charging unit.

In some preferred embodiments, the controller of the aerosol-generating system may be configured to communicate the ambient air quality signal to an external device, such as a user's smartphone, through a short range communications protocol, such as Bluetooth®, and the external device may be configured to communicate the ambient air quality signal to an external server, such as a cloud server, over a network such as the Internet.

The external device or server may be configured to store the data communicated from the aerosol-generating system. The external device or server may be configured to analyse the data communicated from the aerosol-generating system. In some embodiments, the controller of the aerosol-generating system may comprise further sensors and may be configured to collect further data, such as usage data of the aerosol-generating system and geographical location data. The controller may also be configured to communicate the additional data to the external device or server and the external device or server may be configured to analyse the ambient air quality data in conjunction with the additional data, such as usage data and location data.

The aerosol-generating device comprises a heating assembly for heating an aerosol-forming substrate received in the chamber of the device. The heating assembly may be any suitable heating assembly.

The heating assembly may comprise one or more heating elements. In particular, the heating assembly may comprise one or more resistive heating elements. Where the aerosol-forming substrate is a solid substrate, the one or more heating elements may be internal heating elements configured to penetrate the aerosol-forming substrate. The one or more heating elements may be external heating elements, configured for arrangement at or around the aerosol-forming substrate. The heating assembly may comprise one or more internal heating elements and one or more external heating elements.

The one or more heating elements may extend into the chamber for receiving the aerosol-forming substrate. The one or more heating elements may conveniently be shaped as a needle, pin, rod, or blade that may be inserted into the aerosol-forming substrate when the aerosol-forming substrate is received in the chamber.

The one or more heating elements may comprise an electrically resistive material. Suitable electrically resistive materials include but are not limited to: semiconductors such as doped ceramics, electrically "conductive" ceramics (such as, for example, molybdenum disilicide), carbon, graphite, metals, metal alloys and composite materials made of a ceramic material and a metallic material. Such composite materials may comprise doped or undoped ceramics. Examples of suitable doped ceramics include doped silicon carbides. Examples of suitable metals include titanium, zirconium, tantalum and metals from the platinum group. Examples of suitable metal alloys include stainless steel, Constantan, nickel-, cobalt-, chromium-, aluminium- titanium- zirconium-, hafnium-, niobium-, molybdenum-, tantalum-, tungsten-, tin-, gallium-, manganese- and iron-containing alloys, and super-alloys based on nickel, iron, cobalt, stainless steel, Timetal®, iron-aluminium based alloys and iron-manganese-aluminium based alloys. Timetal® is a registered trade mark of Titanium Metals Corporation, 1999 Broadway Suite 4300, Denver Colorado. In composite materials, the electrically resistive material may optionally be embedded in, encapsulated or coated with an insulating material or vice-versa, depending on the kinetics of energy transfer and the external physicochemical properties required. The one or more heating elements may comprise a metallic etched foil insulated between two layers of an inert material. In that case, the inert material may comprise Kapton®, all-polyimide or mica foil. Kapton® is a registered trade mark of E.I. du Pont de Nemours and Company, 1007 Market Street, Wilmington, Delaware 19898, United States of America. A flexible heating element of this type may be conformed to the shape of the chamber and may extend around the periphery of the chamber.

The electric heating element may be formed using a metal having a defined relationship between temperature and resistivity. In such embodiments, the metal may be formed as a track between two layers of suitable insulating materials. An electric heating element formed in this manner may be used both as a heater and a temperature sensor.

In some embodiments, the heating assembly may be an inductive heating assembly. In these embodiments, a susceptor may be arranged in the chamber with the aerosol-forming substrate. In some embodiments, the susceptor may be part of the aerosol-generating device. In some preferred embodiments, the susceptor is comprised in an aerosol-generating article or cartridge comprising the aerosol-forming substrate.

As used herein, a "susceptor element" means a conductive element that heats up when subjected to a changing magnetic field. This may be the result of eddy currents induced in the susceptor element and/or hysteresis losses.

The aerosol-generating device may comprise an inductor coil surrounding at least a portion of the chamber. In these embodiments, the power supply control circuitry of the aerosol-generating device may be configured to generate a fluctuating electromagnetic field within the chamber. Preferably, the inductor coil, power supply and power supply control circuitry may be capable of generating a fluctuating electromagnetic field of between 1 and 30 MHz, for example, between 2 and 10 MHz, for example between 5 and 7 MHz. Preferably the power supply, the power supply control circuitry and inductor coil are capable of generating a fluctuating electromagnetic field having a field strength (H-field) of between 1 and 5 kA m, for example between 2 and 3 kA m, for example about 2.5 kA/m.

The aerosol-generating device comprises a housing. The housing comprises a chamber for receiving an aerosol-forming substrate. The housing may have a proximal end and a distal end. The chamber may be arranged at the proximal end of the device.

The device housing may be elongate. Preferably, the device housing is cylindrical in shape. The device housing may comprise any suitable material or combination of materials. Examples of suitable materials include metals, alloys, plastics or composite materials containing one or more of those materials, or thermoplastics that are suitable for food or pharmaceutical applications, for example polypropylene, polyetheretherketone (PEEK) and polyethylene. Preferably, the material is light and non-brittle.

Preferably the aerosol-generating device is portable. Thee aerosol-generating device may have a length of between approximately 70 millimetres and approximately 120 millimetres. The aerosol-generating device may be a handheld device. In other words, the aerosol-generating device may be sized and shaped to be held in the hand of a user.

In embodiments comprising a charging case, the housing of the charging case may be formed from a similar material to the aerosol-generating device. The chamber of the charging case is configured to receive the aerosol-generating device. Preferably, the charging case is portable. The charging case may be a handheld case. In other words, the charging case may be sized and shaped to be held in the hand of a user.

The aerosol-generating device is configured to interact with an aerosol-forming substrate to generate an aerosol.

As used herein, an aerosol-forming substrate is a substrate capable of releasing volatile compounds that can form an aerosol. Volatile compounds may be released by heating the aerosol-forming substrate.

The aerosol-forming substrate may be a solid aerosol-forming substrate. The solid aerosol-forming substrate may comprise a tobacco-containing material containing volatile tobacco flavour compounds which are released from the substrate upon heating. The aerosol-forming substrate may further comprise an aerosol former that facilitates the formation of a dense and stable aerosol. Examples of suitable aerosol formers are glycerine and propylene glycol.

The solid aerosol-forming substrate may comprise, for example, one or more of: powder, granules, pellets, shreds, spaghettis, strips or sheets containing one or more of: herb leaf, tobacco leaf, fragments of tobacco ribs, reconstituted tobacco, homogenised tobacco, extruded tobacco and expanded tobacco. As used herein, homogenised tobacco refers to material formed by agglomerating particulate tobacco. Homogenised tobacco may be in the form of a sheet. Homogenised tobacco material may have an aerosol-former content of greater than 5% on a dry weight basis. The aerosol-forming substrate may comprises a gathered crimped sheet of homogenised tobacco material. As used herein, the term 'crimped sheet' denotes a sheet having a plurality of substantially parallel ridges or corrugations. The solid aerosol-forming substrate may be in loose form, or may be provided in a suitable container or compartment of the cartridge.

The aerosol-forming substrate may be a liquid aerosol-forming substrate. The liquid aerosol-forming substrate may comprise nicotine. The nicotine containing liquid aerosol-forming substrate may be a nicotine salt matrix. The liquid aerosol-forming substrate may comprise tobacco. The liquid aerosol-forming substrate may comprise a tobacco-containing material containing volatile tobacco flavour compounds, which are released from the aerosol-forming substrate upon heating. The liquid aerosol-forming substrate may comprise homogenised plant-based material. The liquid aerosol-forming substrate may comprise one or more aerosol-formers. An aerosol-former is any suitable known compound or mixture of compounds that, in use, facilitates formation of a dense and stable aerosol and that is substantially resistant to thermal degradation at the temperature of operation of the system. Examples of suitable aerosol formers include glycerine and propylene glycol. The liquid aerosol-forming substrate may comprise water, solvents, ethanol, plant extracts and natural or artificial flavours.

The aerosol-forming substrate may comprise a gel. At room temperature, the gel may have a stable size and shape and may not flow. The gel may comprise a thermoreversible gel. This means that the gel will become fluid when heated to a melting temperature and will set into a gel again at a gelation temperature. The gelation temperature is preferably at or above room temperature and atmospheric pressure. The melting temperature is preferably higher than the gelation temperature. Preferably the melting temperature of the gel is above 50 degrees Celsius, or 60 degrees Celsius or 70 degrees Celsius and more preferably above 80 degrees Celsius. The melting temperature in this context means the temperature at which the gel is no longer solid and begins to flow. Preferably, the gel comprises agar or agarose or sodium alginate. The gel may comprise Gellan gum. The gel may comprise a mixture of materials. The gel may comprise water.

The aerosol-forming substrate may have a vaporisation temperature of between about 70 degrees Celsius to about 230 degrees Celsius. The aerosol-generating system may be configured to heat the aerosol-forming substrate to an average temperature of between about 60° C. and about 240° C.

According to a second aspect of the invention, there is provided an aerosol-generating device comprising: a housing having a chamber for receiving an aerosol-forming substrate; and a heating arrangement for heating the aerosol-forming substrate when the aerosol-forming substrate is received in the chamber. The aerosol-generating device further comprises: an ambient air quality sensor arranged to sense a property of the ambient air in the vicinity of the device; and a controller connected to the ambient air quality sensor, the controller being configured to receive ambient air quality readings from the ambient air quality sensor and output an ambient air quality signal based on one or more of the readings of the ambient air quality sensor.

According to a third aspect of the invention, there is provided a charging case for an aerosol-generating system, the charging case comprising: a housing comprising a chamber for receiving an aerosol-generating device; and power transfer circuitry configured for transferring power to a power supply of an aerosol-generating device when an aerosol-generating device is received in the chamber. The charging case further comprises: an ambient air quality sensor arranged to sense a property of the ambient air in the vicinity of the charging case; and a controller connected to the ambient air quality sensor, the controller being configured to receive ambient air quality readings from the ambient air quality sensor and output an ambient air quality signal based on one or more of the readings of the ambient air quality sensor.

According to a fourth aspect of the invention, there is provided a method of operating an aerosol-generating system comprising a heating assembly and an ambient air quality sensor, the method comprising: measuring a property of the ambient air in the vicinity of the system using the ambient air quality sensor; and controlling a supply of power to the heating assembly based on one or more measurements of ambient air quality from the ambient air quality sensor.

For the avoidance of doubt, features described above in relation to one aspect of the invention may also be applicable to other aspects of the invention. In particular, any feature described in relation to the first aspect may be equally applicable to the second, third and fourth aspects, any feature described in relation to the second aspect may be equally applicable to the first, third and fourth aspects, any feature described in relation to the third aspect may be equally applicable to the first, second and fourth aspects and any feature described in relation to the fourth aspect may be equally applicable to the first, second and third aspects.

Embodiments of the invention will now be described, by way of example only, with reference to the accompanying drawings, in which.

Figure 1:
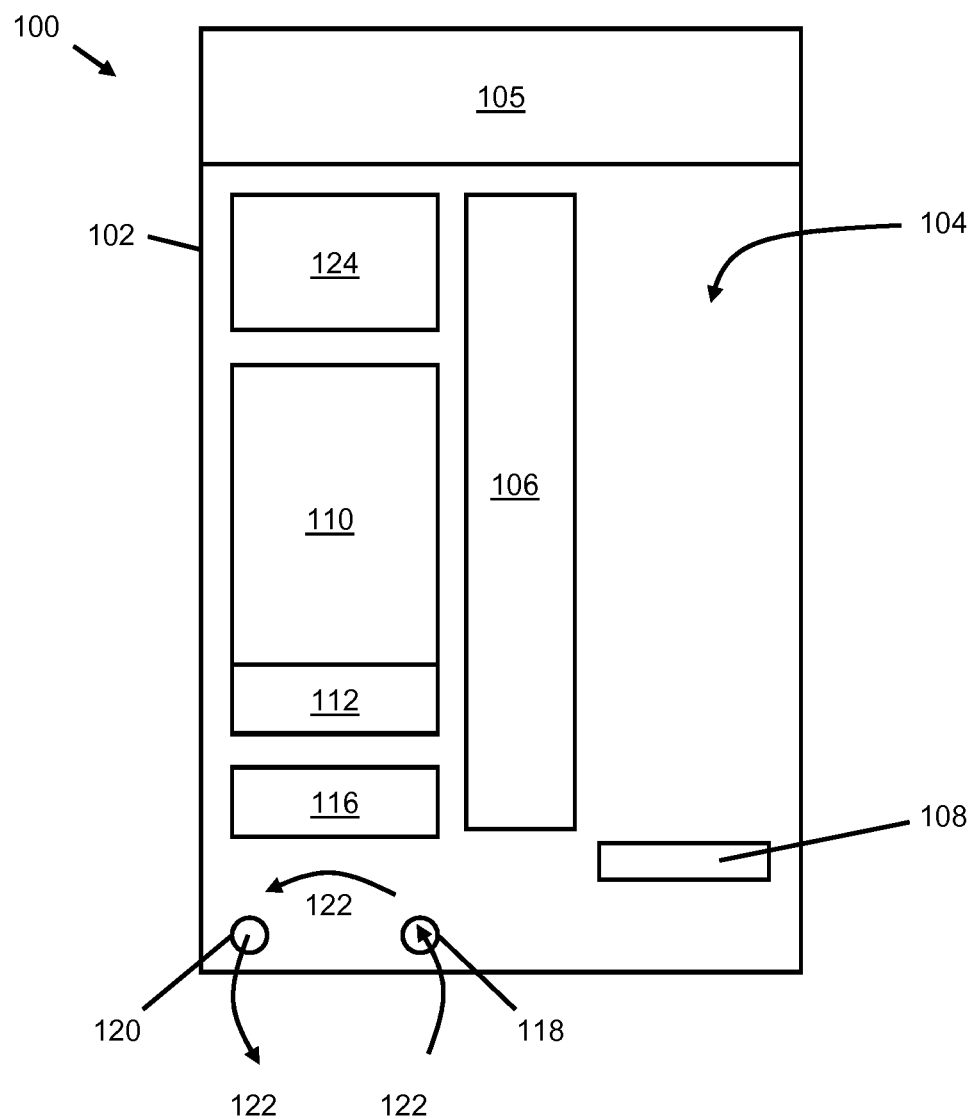
FIG. 1 shows a charging case having an ambient air quality sensor in accordance with a first embodiment of the present invention.

FIG. 1 shows a schematic illustration of a charging unit for an aerosol-generating system according to a first embodiment of the present invention. The charging unit shown in FIG. 1 is a charging case 100. The charging case 100 is a portable case having a housing 102 that is shaped and sized to be grasped in a hand of a user and to fit into a pocket of a user's clothing. The housing 102 is generally a rectangular cuboid having a length of about 20 mm, a width of about 50 mm and a height of about 110 mm.

The housing 102 comprises a chamber 104 for receiving an aerosol-generating device. The chamber 104 is open at a proximal end of the housing 102 to receive an aerosol-generating device and is closed at a distal end of the housing 102, opposite the proximal end. A lid 105 is pivotally attached to the proximal end of the housing 102, via a hinge, and is configured to cover the open end of the chamber 104 when pivoted to a closed position and to reveal the open end of the chamber 104 when pivoted to an open position.

A power supply 106, in the form of a lithium-ion battery with a capacity of about 2900 milliampere-hours (mAh), is housed within the housing 102.

An electrical connector 108 is arranged at the closed distal end of the chamber 104 for receiving the aerosol-generating device. The electrical connector 108 connected to the power supply 106 and is arranged to electrically connect with a corresponding electrical connector of an aerosol-generating device when an aerosol-generating is fully received in the chamber 104.

A controller 110 is also housed within the housing 102. The controller 110 is connected to the power supply 106 and to the electrical connector 108 and is configured to control the supply of power from the power supply 106 to the electrical connector 108.

The controller 110 and electrical connector 108 are configured to supply electrical power to an aerosol-generating device received in the chamber 104 and are also configured to communicate with the aerosol-generating device, to transfer data to the aerosol-generating device and to receive data from the aerosol-generating device.

The controller 110 comprises a microprocessor (not shown) and also comprises a communication interface 112, which in this embodiment comprises a telemetry circuit and an antenna for bidirectional communication with an external device or server. In this embodiment, the communication 112 interface is a wireless interface using Bluetooth® protocol to communicate with an extremal device or server. Typically, the communication interface 112 is configured to communicate with a user's smartphone.

In accordance with the present invention, an ambient air quality sensor 116 is also housed within the housing 102 of the case 100. In this embodiment, the ambient air quality sensor 116 is comprised of a plurality of air quality sensors including: gas sensors for sensing carbon monoxide concentration (CO) and volatile organic compound (VOC) concentration; a fine particulate matter sensor; a humidity sensor adapted to sense the relative humidity of the ambient air around the case, including the temperature of the ambient air; and an ambient pressure sensor. It will be appreciated that in some embodiments the ambient air quality sensor 116 may further include further gas sensors for sensing: nitrogen dioxide (NO2) concentration; carbon dioxide (CO2) concentration; and oxygen (O2) concentration.

Advantageously, the ambient air sensor 116 is arranged towards the distal end of the housing 102, opposite the open end of the chamber 104 and the lid 105 at the proximal end, and at the opposite side of the housing 102 to the chamber 104. This arrangement positions the ambient air sensor 116 as far as possible away from an aerosol-generating device received in the chamber 104. This arrangement is advantageous, as the aerosol-generating device may have been used recently when it is inserted into the case 100 and may still be generating a small amount of aerosol when it is inserted into the case. In this scenario, the aerosol generated by the device may affect the ambient air quality readings of the sensor 116 if the ambient air received by the sensor 116 comprises aerosol generated by the device. In addition, an aerosol-generating device may be configured to perform a cleaning routine when inserted into the chamber, which may comprise supplying a relatively high power to the heater to burn off unwanted residue by pyrolysis. The products from the pyrolysis may also affect the ambient air quality reading from the sensor 116 if the ambient air received by the sensor 116 comprises some of the pyrolysis products.

A first opening 118 is provided in the housing, close to the ambient air quality sensor 116. The first opening 118 is arranged to enable ambient air in the vicinity of the case to enter the housing 102 and reach the ambient air quality sensor 116. A second opening 120 is also provided in the housing 102 close to the ambient air quality sensor 116. The second opening 120 is arranged to enable ambient air received by the ambient air quality sensor 116 to exit the housing 102. As such, an airflow pathway 122 is formed through the housing 102 from the first opening 118, over the ambient air quality sensor 116, to the second opening 120.

The controller 110 of the case 100 is connected to the ambient air quality sensor 116, and is configured to receive ambient air quality readings from the ambient air quality sensor 116. The controller 110 is configured to periodically take readings from the ambient air quality sensor 116. The readings from the ambient air quality sensor 116 comprise information including: carbon monoxide concentration in the ambient air; volatile organic compound concentration in the ambient air; fine particulate matter concentration in the ambient air; relative humidity, including the temperature, of the ambient air; and the pressure of the ambient air. It will be appreciated that in some embodiments, the readings from the ambient air quality sensor may include additional information, including: carbon dioxide concentration; nitrogen dioxide concentration; and oxygen concentration.

The controller 110 is further configured to output an ambient air quality signal based on one or more of the readings of the ambient air quality sensor 116.

The controller 110 is configured to output a first ambient air quality signal based on one or more of the readings of the ambient air quality sensor to the communication interface 112. The communication interface 112 is configured to communicate the first ambient air quality signal to a user's smartphone over a communications link using Bluetooth® protocol.

It is envisaged that a program may be stored on the user's smartphone for analysing ambient air quality information in the first ambient air quality signal. In some embodiments, the program stored on the user's smartphone may not be configured to analyse the data received in the first ambient air quality signal, but rather may be configured to forward the data or the signal to an external server, such as a cloud server for analysis.

The charging case 100 further comprises a graphical display 124 at an outer surface of the housing 102. The controller 110 is further configured to output a second ambient air quality signal based on one or more readings of the ambient air quality sensor to the display 124. The display 124 is configured to display ambient air quality information contained in the second ambient air quality signal so that a user may receive information about the current air quality in the vicinity of the charging unit 100 from the case itself.

Figure 2:
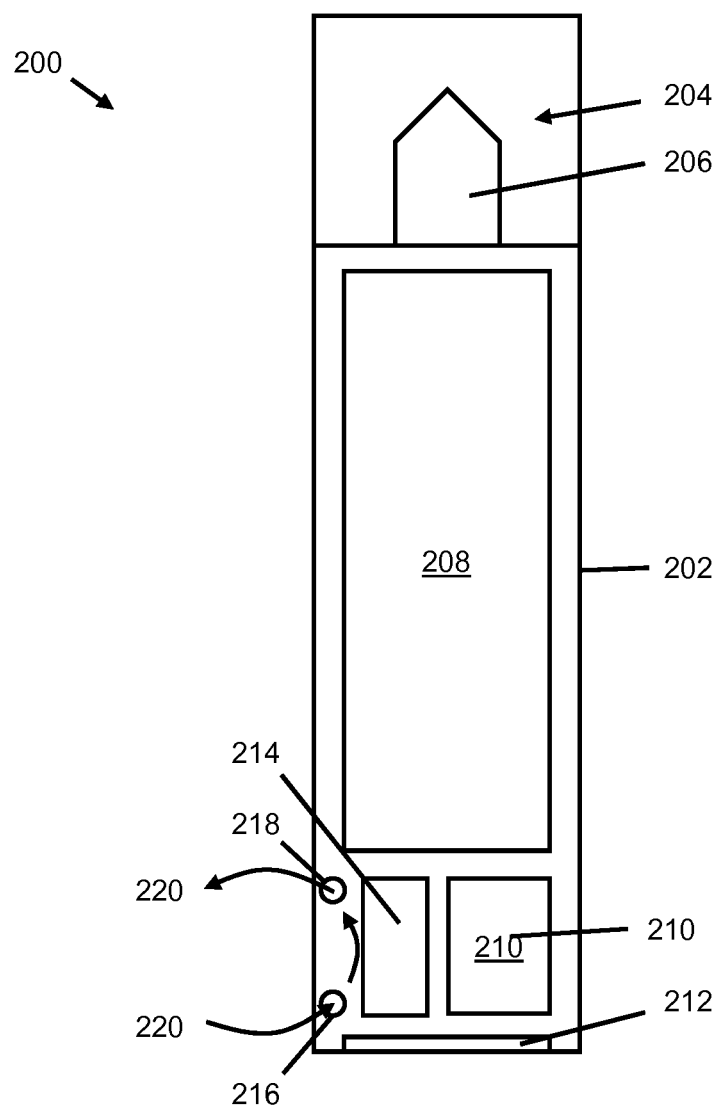
FIG. 2 shows an aerosol-generating device having an ambient air quality sensor in accordance with a second embodiment of the present invention.

FIG. 2 shows a schematic illustration of an aerosol-generating device 200 according to a second embodiment of the present invention. The aerosol-generating device 200 shown in FIG. 2 is a device configured to receive an aerosol-generating article (not shown) comprising a solid aerosol-forming substrate and a filter wrapped together in the form of a rod like a conventional cigarette. The aerosol-generating device 200 is a portable device that is configured to be held in the hand of a user. The aerosol-generating device 200 comprises a housing 202, which is generally cylindrical, having a length of about 90 mm, a diameter of about 14 mm, similar to a conventional cigar. The housing 202 of the device 200 has a shape and dimensions that are generally complimentary to the shape and dimensions of the chamber 104 of the charging case 100 shown in FIG. 1. As such, the device 200 is configured to be received in the chamber 104 of the charging case 100.

An open chamber 204 is provided at a proximal end of the housing 202 of the device 200 for receiving the aerosol-forming substrate of an aerosol-generating article. A heating assembly 206, in the form of a resistive heating blade or pin, extends into the chamber 204 for penetrating into the aerosol-forming substrate of an aerosol-generating article received in the chamber 204.

A power supply 208, in the form of a lithium-ion battery with a capacity of about 120 milliampere-hours, is housed within the housing 202.

A controller 210 is also housed within the housing 202. The controller 210 comprises a microprocessor (not shown). The controller 210 is connected to the heating assembly 206 and the power supply 208, and the controller 210 is configured to control the supply of power from the power supply 208 to the heating assembly 206.

An electrical connector 212 is arranged at a distal end face of the housing 202, opposite the chamber 204. The power supply 208 and the controller 210 are connected to an electrical connector 212. The electrical connector 212 is arranged and configured to electrically connect with the electrical connector 108 at the distal end of the chamber 104 in the housing 102 of the case 100, when the device 200 is received in the chamber 104 of the case 100. As such, when the device 200 is received in the chamber 104 of the case 100, the electrical connector 108 of the case 100 is electrically connected to the electrical connector 212 of the device 200. When the electrical connector 108 of the case 100 and the electrical connector 212 of the device 200 are electrically connected, the controller 110 of the case 100 is configured to supply power from the power supply 106 in the case 100 to the power supply 208 in the device 200 for charging the power supply 208 in the device 200. The controller 210 is configured to control the supply of power from the electrical connector 212 to the power supply 208 for charging the power supply 208. This enables the controller 210 to protect the power supply 208 of the device 200 from overcharging.

The controller 110 of the case 100 and the controller 210 of the device 200 are further configured for bi-directional communication of data via the electrically connected electrical connectors 108, 212.

In accordance with the present invention, an ambient air quality sensor 214 is housed within the housing 202 of the device 200. In this embodiment, the ambient air quality sensor 214 comprises a plurality of air quality sensors including: a gas sensor for sensing carbon monoxide (CO) concentration in the ambient air surrounding the device 200; and a humidity sensor adapted to sense the relative humidity of the ambient air around the device 200, including the temperature of the ambient air. The ambient air quality sensor 214 of the aerosol-generating device 200 comprises fewer sensors than the ambient air quality sensor 116 of the charging case 100, as the size of the aerosol-generating device 200 is significantly smaller than the size of the charging case 100 and the limited space within the housing 202 of the aerosol-generating device 200 limits the number and type of sensors that may be provided in the ambient air quality sensor 214 of the aerosol-generating device 200.

Advantageously, the ambient air sensor 214 is arranged towards the distal end of the housing 202, at the opposite end of the device 200 to the chamber 204 at the proximal end. This arrangement positions the ambient air sensor 214 as far as possible away from the heating assembly 206 and the aerosol generated by the device 200. This arrangement is advantageous, as the aerosol generated by the aerosol-generating device may affect the ambient air quality readings of the sensor 214 if the ambient air received by the ambient air quality sensor 214 comprises aerosol generated by the device 200.

A first opening 216 is provided in the housing 202, close to the ambient air quality sensor 214. The first opening 216 is arranged to enable ambient air in the vicinity of the device to enter the housing 202 and reach the ambient air quality sensor 214. A second opening 218 is also provided in the housing 202 close to the ambient air quality sensor 214. The second opening 218 is arranged to enable ambient air received by the ambient air quality sensor 214 to exit the housing 202. An airflow pathway 220 is formed through the housing 202 from the first opening 216, over the ambient air quality sensor 214, to the second opening 218.

The controller 210 of the device 200 is connected to the ambient air quality sensor 214, and is configured to receive ambient air quality readings from the ambient air quality sensor 214. The controller 210 is further configured to output an ambient air quality signal based on one or more of the readings of the ambient air quality sensor 214.

The controller 210 is configured to output an ambient air quality signal based on one or more of the readings of the ambient air quality sensor 214. In particular, the controller 210 is configured to control the supply of power from the power supply 208 to the heating assembly 206 based on one or more ambient air quality readings from the ambient air quality sensor 214, as described in more detail below with reference to FIG. 4.

The controller 210 may be configured to store the ambient air quality readings from the ambient air quality sensor 214 in a memory (not shown) until the device 200 is received in the charging case 100. The controller 210 may be configured to communicate the stored ambient air quality readings to the controller 110 of the charging case 100 when the device 200 is received in the chamber 104 of the charging case 100.

Figure 3:
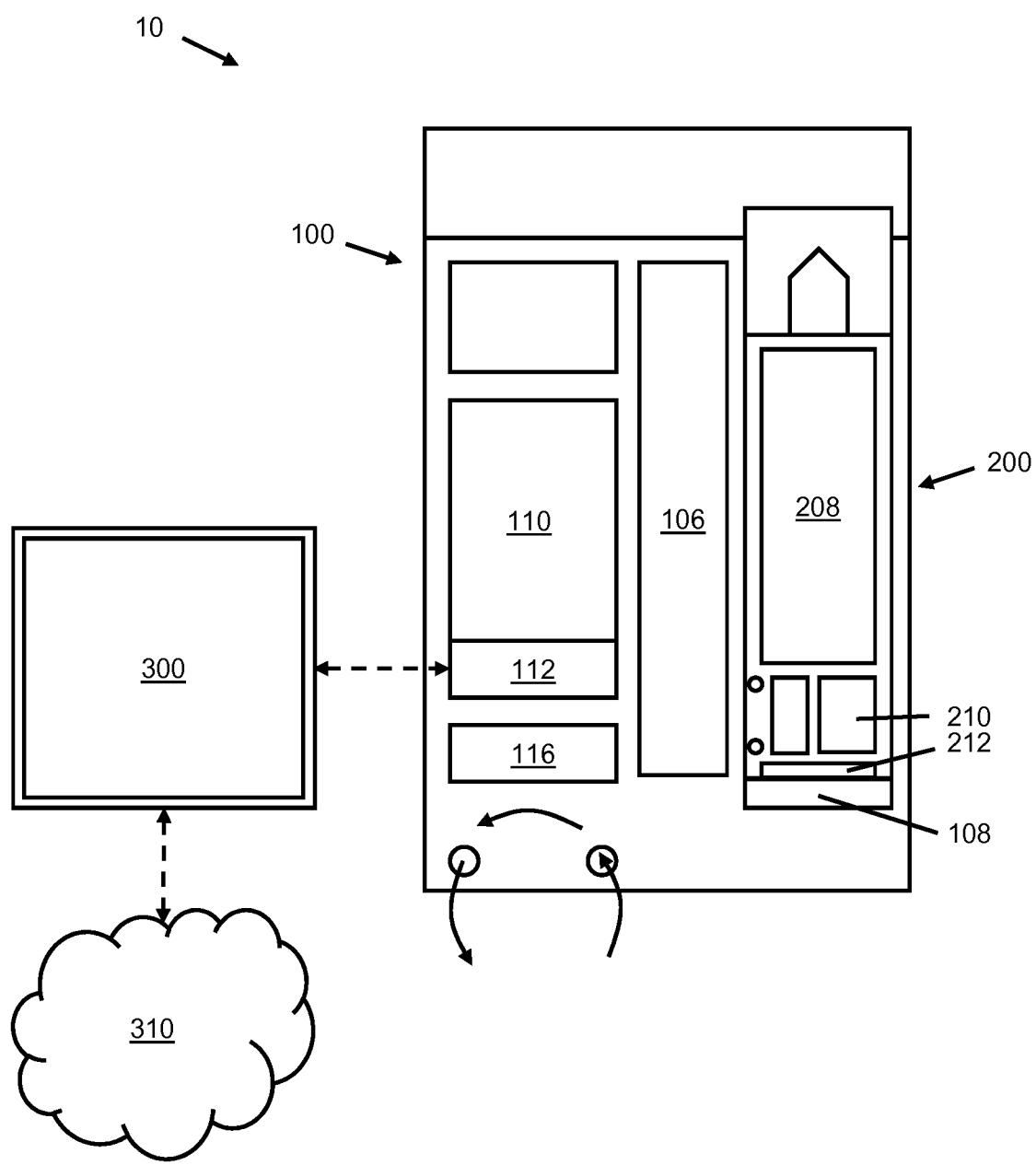
FIG. 3 shows the aerosol-generating device of FIG. 2 received within the charging case of FIG. 1 and the charging case communicating with an external cloud server in accordance with an aspect of the present invention.

FIG. 3 shows a schematic illustration of the aerosol-generating device 200 of FIG. 2 received in the chamber 104 of the charging case 100 of FIG. 1.

When the aerosol-generating device 200 is received in the case 100, the controller 210 of the aerosol-generating device 200 is configured to communicate with the controller 110 of the charging case 100 via the electrically connected electrical connectors 108, 212. In particular, the controller 210 of the device 200 is configured to communicate stored ambient air quality readings to the controller 110 of the case 100.

The controller 210 of the device 200 is also configured to determine when the device 200 is received in the charging case 100, either by interrogating the controller 110 of the case 100 or by determining that the power supply 208 is being charged. The controller 210 of the device 200 is further configured to stop taking ambient air quality readings while the device 200 is received in the chamber 104 of the case 100. The controller 210 is configured to stop taking ambient air quality readings while the device 200 is received in the chamber 104 as the air within the chamber 104 may not be representative of the ambient air in the vicinity of the system. The difference between the air quality in the chamber 104 of the case 100 and the ambient air quality in the vicinity of the system may be particularly large if the controller 210 of the device 200 is configured to perform a cleaning operation, such as supplying power to the heating assembly to burn off residue by pyrolysis, when the device 200 is received in the chamber 104 of the case 100.

FIG. 3 also shows the controller 110 of the charging case 100 communicating with a user's smartphone 300 over a wireless communications link using Bluetooth® protocol.

The controller 110 of the charging case 100 is configured to periodically communicate the first ambient air quality signal to a user's smartphone 300 via the communication interface 112. The controller 110 is further configured to communicate the ambient air quality signal received from the controller 210 of the aerosol-generating device 200 to the user's smartphone 300 over the wireless communications link, via the communication interface 112.

In this embodiment, the user's smartphone is configured to store the received ambient air quality data in the received ambient air quality signals and to periodically communicate the stored ambient air quality data to an external cloud server, via the Internet. The ambient air quality data may be analysed by the cloud server, for example by comparing the ambient air quality data to historic ambient air quality data. The user's smartphone may be further configured to communicate geographical location information to the external cloud server with the ambient air quality data, such that a geographical map of air quality data may be constructed by the cloud server.

Figure 4:
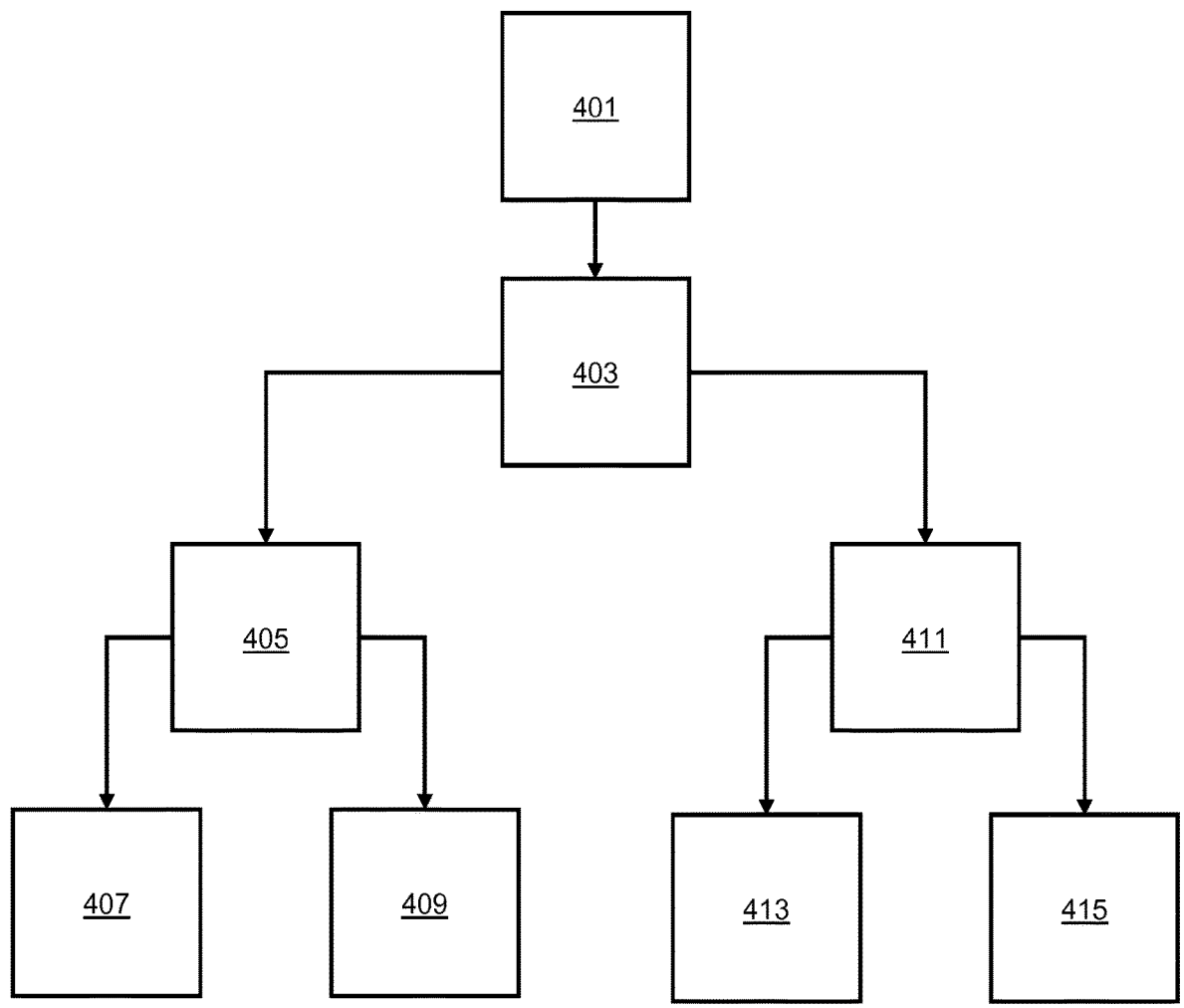
FIG. 4 shows an exemplary logic diagram that the controller of the aerosol-generating device of FIG. 2 is configured to follow.

FIG. 4 shows an exemplary logic diagram that the controller 210 of the aerosol-generating device 200 of FIG. 2 is configured to follow. In other words, FIG. 4 shows an exemplary method of operating an aerosol-generating device having an ambient air quality sensor according to the present invention.

At a first step, 401, the controller 210 is configured to receive an ambient air quality reading from the ambient air quality sensor 214. In this embodiment, the ambient air quality reading includes a carbon monoxide concentration reading and a relative humidity reading.

At a second step, 403, the controller 210 is configured to compare the carbon monoxide concentration reading to a minimum carbon monoxide concentration threshold stored on a lookup table in a memory of the controller 210.

If, at the second step 403, the carbon monoxide concentration reading is determined to be above the predetermined minimum threshold, at a third step, 405, the controller 210 is configured to compare the carbon monoxide concentration reading to a predetermined maximum carbon monoxide concentration threshold stored on the lookup table in the memory of the controller 210.

If, at the third step 405, the carbon monoxide concentration reading is determined to be above the predetermined maximum carbon monoxide concentration threshold, at a fourth step, 407, the controller 210 is configured to prevent the supply of power from the power supply 208 to the heating assembly 206. In other words, the controller 210 is configured to prevent operation of the device 200 if the level of carbon monoxide in the ambient air is above the predetermined maximum threshold.

In some embodiments, the aerosol-generating device 200 may be provided with an alarm, for example, a visual alarm, such as an LED, or an audible alarm, such as a buzzer, and the controller 210 may be configured to send an alarm signal to the alarm to activate the alarm when the controller 20 determines that the measured carbon monoxide concentration is above the predetermined maximum carbon monoxide concentration threshold.

If, at the third step 405, the carbon monoxide concentration reading is determined to be below the predetermined maximum carbon monoxide concentration threshold, at a fifth step, 409, the controller 210 is configured to supply a reduced power profile to the heating assembly 206, such that a lower volume of aerosol may be generated by the device than under normal conditions where the carbon monoxide concentration in the ambient air is below the predetermined minimum threshold. The reduced power profile is stored in the lookup table on the memory of the controller 210

If, at the second step 403, the carbon monoxide concentration reading is determined to be below the predetermined minimum carbon monoxide concentration threshold, at a sixth step, 411, the controller 210 is configured to compare the relative humidity reading to a predetermined humidity threshold stored on the lookup table on the memory of the controller 210.

If, at the sixth step 411, the relative humidity reading is determined to be below the predetermined humidity threshold, the controller 210 is configured to supply a standard power profile to the heating assembly 206 for maintaining the temperature of the heating assembly 206 at a standard temperature profile for generating a standard aerosol for consumption by a user. The standard power profile is stored on the lookup table in the memory of the controller 210.

If, at the sixth step 411, the relative humidity reading is determined to be above the predetermined humidity threshold, the controller 210 is configured to supply an increased power profile to the heating assembly 206 during an initial preheating period, such that the temperature of the heating assembly 206 is raised to a higher temperature than in the standard power profile during the preheating period to vapourise any additional moisture that may be present in the substrate as a result of the humidity. The increased power profile is stored in the lookup table on the memory of the controller 210.

In this way, the controller 210 of the aerosol-generating device 200 is configured to control the supply of power to the heating assembly 206 based on the ambient air quality readings from the ambient air quality sensor.

In this embodiment, the controller 210 is configured to take readings from the ambient air quality sensor 214 before supplying power to the heating assembly 206. As a result, ambient air quality readings are taken before aerosol-generating begins. This further reduces the likelihood of the ambient air sensed by the ambient air quality sensor 214 of the device 200 from including aerosol generated by the aerosol-generating device 200. In addition, by only requiring readings of ambient air quality to be analysed before aerosol-generating begins, the controller may minimise the use of processor resources in determining ambient air quality for an aerosol-generating experience, reducing the power required to operate the device and saving battery life.

The exemplary embodiments described above are illustrative but are not limiting. In view of the above discussed exemplary embodiments, other embodiments consistent with the above exemplary embodiments will now be apparent to one of ordinary skill in the art.

The invention claimed is:

1. An aerosol-generating system, comprising:
an aerosol-generating device comprising:
a housing having a chamber configured to receive an aerosol-forming substrate, the chamber being arranged at a proximal end of the aerosol-generating device,
a heating assembly configured to heat the aerosol-forming substrate when the aerosol-forming substrate is received in the chamber,
an ambient air quality sensor arranged to sense a property of ambient air in a vicinity of the aerosol-generating system, the ambient air quality sensor being configured to sense one or more of: carbon monoxide, volatile organic compounds, carbon dioxide, fine particulate matter, nitrogen dioxide, dioxygen, pressure, and nicotine, and the ambient air quality sensor being further arranged at a distal end of the device, opposite the proximal end, and
a controller connected to the ambient air quality sensor, configured to receive ambient air quality readings from the ambient air quality sensor and to output an ambient air quality signal based on one or more of the ambient air quality readings of the ambient air quality sensor,
wherein the ambient air quality sensor is substantially isolated from the chamber of the aerosol-generating device,
wherein the ambient air quality sensor is further arranged within the housing, and
wherein the housing further comprises a first opening configured to enable ambient air to enter the housing to reach the ambient air quality sensor, and a second opening configured to enable ambient air to exit the housing, an airflow pathway being formed through the housing from the first opening, over the ambient air quality sensor, to the second opening.

2. The aerosol-generating system according to claim 1, wherein the controller is arranged on or in the housing of the aerosol-generating device.

3. The aerosol-generating system according to claim 1, wherein:
the aerosol-generating device further comprises a power supply and power supply control circuitry configured to control a supply of power from the power supply to the assembly, and
the power supply control circuitry is configured to receive the ambient air quality signal from the controller and control the supply of power from the power supply to the heating assembly based on the ambient air quality signal.

4. The aerosol-generating system according to claim 3, wherein the power supply control circuitry is further configured to compare the ambient air quality signal from the ambient air quality sensor to a predetermined ambient air quality condition and to prevent the supply of power from the power supply to the heating assembly when the ambient air quality signal is outside of the predetermined ambient air quality condition.

5. An aerosol-generating system, comprising:
an aerosol-generating device comprising:
a housing having a chamber configured to receive an aerosol-forming substrate,
a heating assembly configured to heat the aerosol-forming substrate when the aerosol-forming substrate is received in the chamber, and
a power supply housed in the housing; and
a charging unit comprising:
power transfer circuitry configured to transfer power to the power supply of the aerosol-generating device;
an ambient air quality sensor arranged to sense a property of ambient air in a vicinity of the aerosol-generating system, the ambient air quality sensor being configured to sense one or more of: carbon monoxide, volatile organic compounds, carbon dioxide, fine particulate matter, nitrogen dioxide, dioxygen, pressure, and nicotine, and
a controller connected to the ambient air quality sensor, configured to receive ambient air quality readings from the ambient air quality sensor and to output an ambient air quality signal based on one or more of the ambient air quality readings of the ambient air quality sensor.

6. The aerosol-generating system according to claim 5, wherein the ambient air quality sensor and the controller are arranged on or in the charging unit.

7. The aerosol-generating system according to claim 5, wherein:
the charging unit is a charging case having a chamber configured to receive the aerosol-generating device and the power supply housed in the housing, and
the power transfer circuitry is configured to transfer power from the power supply of the charging case to the power supply of the aerosol-generating device when the aerosol-generating device is received in the chamber of the charging case.

8. The aerosol-generating system according to claim 7, wherein the ambient air quality sensor is arranged in the housing of the charging case, and
wherein the housing of the charging case comprises at least one opening configured to enable ambient air to enter the housing and to reach the ambient air quality sensor.

9. The aerosol-generating system according to claim 5, wherein the aerosol-generating device further comprises a first ambient air quality sensor and the charging unit further comprises a second ambient air quality sensor.

10. The aerosol-generating system according to claim 1, wherein the ambient air quality sensor comprises at least one of: an electrochemical sensor, a chemical resistive sensor, a metal-oxide-semiconductor (MOS) sensor, a catalytic sensor, a gas spectrometer, and a nicotine sensor.

11. The aerosol-generating system according to claim 1, wherein the aerosol-generating system further comprises a display connected or connectable to the controller and being configured to receive the ambient air quality signal from the controller and to display ambient air quality information based on the ambient air quality signal.

12. The aerosol-generating system according to claim 1, wherein the aerosol-generating system further comprises a wireless transceiver configured to transmit the ambient air quality signal.

13. An aerosol-generating device, comprising:
a housing having a chamber configured to receive an aerosol-forming substrate, the chamber being arranged at a proximal end of the aerosol-generating device; and a heating assembly configured to heat the aerosol-forming substrate when the aerosol-forming substrate is received in the chamber;

an ambient air quality sensor arranged to sense a property of ambient air in a vicinity of the device, the ambient air quality sensor being configured to sense one or more of: carbon monoxide, volatile organic compounds, carbon dioxide, fine particulate matter, nitrogen dioxide, dioxygen, pressure, and nicotine, and the ambient air quality sensor being further arranged at a distal end of the device, opposite the proximal end; and a controller connected to the ambient air quality sensor, configured to receive ambient air quality readings from the ambient air quality sensor and to output an ambient air quality signal based on one or more of the readings of the ambient air quality sensor, wherein the ambient air quality sensor is substantially isolated from the chamber of the aerosol-generating device, wherein the ambient air quality sensor is further arranged within the housing, and wherein the housing further comprises a first opening configured to enable ambient air to enter the housing to reach the ambient air quality sensor, and a second opening configured to enable ambient air to exit the housing, an airflow pathway being formed through the housing from the first opening, over the ambient air quality sensor, to the second opening.

14. A charging case for an aerosol-generating system, the charging case comprising:

a housing comprising a chamber configured to receive an aerosol-generating device;

power transfer circuitry configured to transfer power to a power supply of an aerosol-generating device when the aerosol-generating device is received in the chamber;

an ambient air quality sensor arranged to sense a property of ambient air in a vicinity of the charging case, the ambient air quality sensor being configured to sense one or more of: carbon monoxide, volatile organic compounds, carbon dioxide, fine particulate matter, nitrogen dioxide, dioxygen, pressure, and nicotine; and a controller connected to the ambient air quality sensor, configured to receive ambient air quality readings from the ambient air quality sensor and to output an ambient air quality signal based on one or more of the readings of the ambient air quality sensor.

* * * * *